US011725055B2

(12) United States Patent
Estelles et al.

(10) Patent No.: US 11,725,055 B2
(45) Date of Patent: Aug. 15, 2023

(54) MONOCLONAL ANTIBODIES TARGETING KILLER IMMUNOGLOBULIN-LIKE RECEPTOR (KIR) FAMILY SIGNALING

(71) Applicant: Trellis Bioscience, LLC, Redwood City, CA (US)

(72) Inventors: Angeles Estelles, Belmont, CA (US); Mikhail Gishizky, Napa, CA (US); Stefan Ryser, Menlo Park, CA (US); Lawrence M. Kauvar, San Francisco, CA (US)

(73) Assignee: Trellis Bioscience, LLC

( * ) Notice: Subject to any disclaimer, the term of this patent is extended or adjusted under 35 U.S.C. 154(b) by 441 days.

(21) Appl. No.: 17/091,526

(22) Filed: Nov. 6, 2020

(65) Prior Publication Data
US 2021/0054075 A1    Feb. 25, 2021

Related U.S. Application Data

(62) Division of application No. 15/619,327, filed on Jun. 9, 2017, now Pat. No. 10,858,431.

(60) Provisional application No. 62/356,815, filed on Jun. 30, 2016.

(51) Int. Cl.
*C07K 16/28* (2006.01)
*A61K 39/395* (2006.01)
*A61K 45/06* (2006.01)

(52) U.S. Cl.
CPC ...... *C07K 16/2803* (2013.01); *A61K 39/3955* (2013.01); *A61K 45/06* (2013.01); *C07K 2317/10* (2013.01); *C07K 2317/21* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 9,018,366 B2 | 4/2015 | Padkær | |
| 2011/0293561 A1 | 12/2011 | Romagne | |
| 2015/0376275 A1 | 12/2015 | Romagne | |
| 2016/0046712 A1 | 2/2016 | Padkær | |

FOREIGN PATENT DOCUMENTS

| | | |
|---|---|---|
| WO | 2006003179 | 1/2006 |
| WO | 2012160448 | 11/2012 |
| WO | 2016069589 | 5/2016 |
| WO | 2016130950 | 8/2016 |

OTHER PUBLICATIONS

Khan, et al., "Adjustable Locks and Flexible Keys: Plasticity of Epitope—Paratope Interactions in Germline Antibodies", 2014, J. Immunol. vol. 192:5398-5405.
Kohrt, et al., "Anti-KIR antibody enhancement of anti-lymphoma activity of natural killer cells as monotherapy and in combination with anti-CD 20 antibodies", Blood, (Jan. 30, 2014), vol. 123, No. 5, pp. 678-686, XP055447753.
Mariuzza, et al., "The Strutural Basis of Antigent-Antibody Recognition", 1987, Ann. Rev. Biophy. Chem. vol. 16: 139-59.
Rudikoff, et al., "Single amino acid substitution altering antigen-binding specificity", 1982, PNAS, vol. 79: 1979-1983.
Sola, et al., "Anti-tumoral efficacy of therapeutic human anti-KIR antibody (Lirilumab/BMS-986015/IPH2102) in a preclinical xenograft tumor model", Journal for ImmunoTherapy of Cancer, (Nov. 7, 2013), vol. 1, No. 1, p. P40, XP021167250.

*Primary Examiner* — Amy E Juedes
(74) *Attorney, Agent, or Firm* — FisherBroyles, LLP; Jason M. Pass

(57) ABSTRACT

Monoclonal antibodies derived from the native human repertoire that bind the extracellular portion of Killer IgG Receptor (KIR) and pharmaceutical and veterinary compositions thereof are useful in treating cancer in human and other subjects.

4 Claims, No Drawings

Specification includes a Sequence Listing.

SEQUENCE LISTING

<160> NUMBER OF SEQ ID NOS: 8

<210> SEQ ID NO 1
<211> LENGTH: 120
<212> TYPE: PRT
<213> ORGANISM: Artificial Sequence
<220> FEATURE:
<223> OTHER INFORMATION: Synthetic: TRL8504 VH

<400> SEQUENCE: 1

Gln Val Gln Leu Val Glu Ser Gly Gly Gly Val Val Arg Pro Gly Arg
1               5                   10                  15

Ser Leu Arg Leu Ser Cys Ala Ala Ser Gly Phe Thr Phe Asn Arg Phe
                20                  25                  30

Ala Met His Trp Val Arg Gln Ala Pro Gly Lys Gly Leu Glu Trp Val
            35                  40                  45

Ser Val Ile Ser Tyr Asp Gly His Asn Lys Tyr Tyr Ile Asp Ser Val
        50                  55                  60

Lys Gly Arg Phe Thr Ile Ser Arg Asp Asp Ser Lys Asn Thr Leu His
65                  70                  75                  80

Leu Gln Met Asn Ser Leu Arg Pro Glu Asp Thr Ala Val Tyr Tyr Cys
                85                  90                  95

Ala Arg Ala Arg Asp Asp Gly Arg Gly Ile Phe Asp Tyr Trp Gly Gln
            100                 105                 110

Gly Ile Leu Val Thr Val Ser Ser
        115                 120

<210> SEQ ID NO 2
<211> LENGTH: 114
<212> TYPE: PRT
<213> ORGANISM: Artificial Sequence
<220> FEATURE:
<223> OTHER INFORMATION: Synthetic: TRL8504 VL (kappa)

<400> SEQUENCE: 2

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

```
Ser Asn Asn Arg Asn Tyr Leu Ala Trp Tyr Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr His Ser Ile Pro Leu Thr Phe Gly Gly Gly Thr Lys Val Glu Ile
                100                 105                 110

Lys Arg
```

<210> SEQ ID NO 3
<211> LENGTH: 129
<212> TYPE: PRT
<213> ORGANISM: Artificial Sequence
<220> FEATURE:
<223> OTHER INFORMATION: Synthetic: TRL8507 VH

<400> SEQUENCE: 3

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asn Tyr
             20                  25                  30

Gly Met His Trp Val Arg Gln Ala Pro Gly Lys Gly Leu Glu Trp Val
         35                  40                  45

Ala Val Ile Ser Phe Asp Gly Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Gly Tyr Phe Asp Ser Ser Gly Tyr Phe Tyr Pro Tyr Tyr
                100                 105                 110

Tyr Tyr Gly Met Asp Val Trp Gly Gln Gly Thr Thr Val Thr Val Ser
        115                 120                 125

Ser
```

<210> SEQ ID NO 4
<211> LENGTH: 108
<212> TYPE: PRT
<213> ORGANISM: Artificial Sequence
<220> FEATURE:
<223> OTHER INFORMATION: Synthetic: TRL8507 VL (lambda)

<400> SEQUENCE: 4

```
Asp Ile Glu Leu Thr Gln Ala Pro Ser Val Ser Val Ser Pro Gly Gln
 1               5                  10                  15

Thr Ala Arg Ile Thr Cys Ser Gly Asp Ala Leu Pro Lys Glu Tyr Ala
             20                  25                  30

Tyr Trp Tyr Gln Gln Lys Pro Gly Gln Ala Pro Val Leu Val Ile Tyr
         35                  40                  45

Lys Asp Ser Glu Arg Pro Ser Gly Ile Pro Glu Arg Phe Ser Gly Ser
     50                  55                  60

Ser Ser Gly Thr Thr Val Thr Leu Thr Ile Ser Gly Val Gln Ala Glu
 65                  70                  75                  80

Asp Glu Gly Asp Tyr Tyr Cys Gln Ser Ala Asp Ser Ser Gly Thr His
```

```
                      85                  90                  95

Val Val Phe Gly Gly Gly Thr Lys Leu Thr Val Leu
                100                 105

<210> SEQ ID NO 5
<211> LENGTH: 114
<212> TYPE: PRT
<213> ORGANISM: Artificial Sequence
<220> FEATURE:
<223> OTHER INFORMATION: Synthetic: TRL8605 VH

<400> SEQUENCE: 5

Gln Val Gln Leu Val Gln Ser Gly Gly Val Val Gln Pro Gly Arg
1               5                   10                  15

Ser Leu Arg Leu Ser Cys Ala Val Ser Gly Phe Thr Phe Ser Ser Tyr
                20                  25                  30

Gly Met His Trp Val Arg Gln Ala Pro Gly Lys Gly Leu Glu Trp Val
            35                  40                  45

Thr Ile Ile Ser Tyr Asp Gly Ser Asn Tyr Asp Tyr Ala Asp Ser Val
        50                  55                  60

Lys Gly Arg Phe Thr Ile Ser Arg Asp Asn Ser Lys Asn Met Val Tyr
65                  70                  75                  80

Leu Gln Met Asn Ser Leu Arg Ala Asp Asp Thr Ala Val Tyr Tyr Cys
                85                  90                  95

Ala Lys Asp Gly Phe Asp Tyr Trp Gly Gln Gly Thr Leu Val Thr Val
                100                 105                 110

Ser Ser

<210> SEQ ID NO 6
<211> LENGTH: 114
<212> TYPE: PRT
<213> ORGANISM: Artificial Sequence
<220> FEATURE:
<223> OTHER INFORMATION: Synthetic: TRL8605 VL (kappa)

<400> SEQUENCE: 6

Asp Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Arg Thr Tyr Leu Ala Trp Phe Gln Gln Lys Ser Gly Gln
            35                  40                  45

Pro Pro Lys Leu Leu Ile Tyr Trp Ala Ser Thr Arg Gln Ser Gly Val
        50                  55                  60

Ala Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Phe Thr Phe Gly Pro Gly Thr Arg Val Asp Phe
                100                 105                 110

Lys Arg

<210> SEQ ID NO 7
<211> LENGTH: 122
<212> TYPE: PRT
<213> ORGANISM: Artificial Sequence
<220> FEATURE:
<223> OTHER INFORMATION: Synthetic: TRL8608 VH
```

```
<400> SEQUENCE: 7

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Ser Tyr
            20                  25                  30

Tyr Met His Trp Leu Arg Gln Ala Pro Gly Gln Gly Leu Glu Trp Met
        35                  40                  45

Gly Val Ile Asn Pro Thr Asp Gly Ser Thr Ser Tyr Ala Gln Lys Phe
    50                  55                  60

His Gly Arg Val Thr Met Thr Arg Val Thr Ser Thr Ser Thr Val Tyr
65                  70                  75                  80

Met Asp Leu Ser Ser Leu Arg Ser Asp Asp Thr Ala Met Tyr Tyr Cys
                85                  90                  95

Ala Lys Ala His Ile His Ala Ala Glu Gly Trp Phe Asp Pro Trp
            100                 105                 110

Gly Gln Gly Thr Leu Val Thr Val Ser Ser
        115                 120

<210> SEQ ID NO 8
<211> LENGTH: 114
<212> TYPE: PRT
<213> ORGANISM: Artificial Sequence
<220> FEATURE:
<223> OTHER INFORMATION: Synthetic: TRL8608 VL (kappa)

<400> SEQUENCE: 8

Asp Ile Glu Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Asn
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Phe Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Val Pro Trp Thr Phe Gly Gln Gly Thr Lys Val Glu Ile
            100                 105                 110

Lys Arg
```

MONOCLONAL ANTIBODIES TARGETING KILLER IMMUNOGLOBULIN-LIKE RECEPTOR (KIR) FAMILY SIGNALING

CROSS-REFERENCE TO RELATED APPLICATIONS

This application is a divisional application claiming priority to U.S. application Ser. No. 15/619,327, filed 9 Jun. 2017, which claims Opriority from U.S. provisional application 62/356,815 filed 30 Jun. 2016. The contents of the above application are incorporated by reference herein in their entirety.

IN THE SEQUENCE LISTING

Please insert the sequence listing submitted herewith as an ASCII .txt file into the above-captioned application. A computer readable form of the sequence listing (in ASCII .txt format) electronically filed via EFS—Web accompanies this response. Applicant respectfully requests consideration and entry of the sequence listing.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 12774-134US2_ST25.txt, date recorded: Nov. 6, 2020, size: 10 KB).

FIELD OF THE INVENTION

The invention relates to agents and methods that act as immune checkpoint modulators (ICM). More specifically, it relates to antibodies that augment killing of tumor cells by Natural Killer cells (NK cells) by reducing inhibitory Killer Immunoglobulin-like Receptor (KIR) family signaling. The invention also relates to pharmaceutical use of such agents and to methods of manufacturing such agents using transfected cell lines.

BACKGROUND ART

Over the past 20 years, discovery of antibody therapeutics for cancer has focused on proteins associated with tumor cells (also known as tumor-associated antigens). Several such anti-tumor antibody drugs have been commercialized, including those targeting VEGF, Her2, EGFR, and CD20. The need for an exogenous source of these antibodies arises from the high variability in the natural immune response to tumor associated antigens. This variability is due in part to tumor secretion of immunosuppressive factors.

Over the past 5 years, a new class of cancer therapeutics has been developed clinically that act by stimulating the immune system, thereby improving the body's natural ability to fight cancer. This class of therapeutics is known as immune checkpoint modulators (ICM). So far, all of the drugs in this class have themselves been antibodies, including the approved drugs Yervoy™ (ipilimumab), Opdivo™ (nivolumab) and Keytruda™ (pembrolizumab) whose respective targets are CTLA-4, PD-1 and PD-L1. These ICM antibodies work by temporarily lifting a brake on the immune system thereby counteracting tumor induced immune suppression. The ICM drugs have proven to be particularly effective in treating melanoma, which frequently secretes immune suppressing factors.

Increased efficacy from combinations of these first generation ICM antibodies has been observed clinically, but this is accompanied by increased toxicity that resembles autoimmune disease. Further improvement thus depends on identifying combinations of agents that boost anti-tumor immunity while minimizing the adverse consequences of immune system stimulation. Monoclonal antibodies based on native human antibodies with ICM activity are of particular interest, as they have been pre-selected naturally to be well tolerated. Such antibodies may preferentially bind to particular ICM targets, or to particular epitopes on those targets. More than 20 potential ICM targets have been described in the scientific literature.

The ICM targets of the present invention are members of the Killer Immunoglobulin-like Receptor (KIR) family, which comprises 17 genes (including two pseudogenes).

U.S. Pat. No. 9,018,366 discloses certain monoclonal antibodies against the KIR family derived from murine hybridomas. The antibodies disclosed here, derived from the natural human immune repertoire, are distinct from those described in the '366 patent.

DISCLOSURE OF THE INVENTION

The present invention provides monoclonal antibodies (mAbs) based on rare antibodies (defined by specificity and affinity) within the memory B-cell compartment of the human immune system. Surprisingly the native antibodies have been identified in and cloned from healthy blood donors with no known cancer, i.e., the pharmacological approach represented by administration of ICM antibodies appears to have a natural counterpart, consistent with the long standing immune surveillance concept that in healthy individuals incipient tumors are eliminated by the immune system. The low frequency of memory B cells making high affinity antibodies to ICM targets also suggests that the natural ICM mechanism is transient, leaving a footprint in the memory B cell repertoire without leading to long term autoimmune disease.

The mAbs of the invention are thus based on native human antibodies to the KIR family expressed on Natural Killer cells (NK cells). Many tumors down-regulate expression of Major Histocompatibility Complex (MHC) class I molecules in order to escape cytolytic T cell attack. However, this increases their susceptibility to lysis by NK cells through a process known as "missing self" recognition. Engagement of human MHC (HLA antigens) by some KIR family members results in inhibitory signaling that prevents NK cell-mediated cytotoxicity, a useful trait with regard to healthy cells. Antibodies that block the binding of inhibitory KIR to their HLA ligands are useful to enhance NK mediated killing of tumor cells.

In one aspect, the invention is directed to monoclonal antibodies recombinantly produced and derived from particular domains of isolated native human antibodies that target members of the KIR family. The antibodies of the invention thus may include variable regions of the isolated antibodies, but, in general, when produced in the form of complete antibodies contain a generic constant region not native to the isolated forms. In addition, the mAbs may be in the form only of antigen binding fragments including $F_v$ antibodies. They may also be modified to resemble antibodies from any particular species, i.e., "specie-ized" including species of veterinary interest such as dogs, cats, livestock, such as bovine, ovine and porcine, as well as equine species.

The invention is also directed to recombinant materials for production of these antibodies, methods of their production, and methods of use to treat cancer. Thus, pharmaceutical compositions and veterinary compositions are also included.

MODES OF CARRYING OUT THE INVENTION

Human-related antibodies such as those disclosed here are particularly favorable from both an efficacy perspective (having been based on those cloned from healthy donors) and a safety perspective (reduced chance of off-target reactivity that would create toxicity as compared to mAbs cloned from recombinant libraries, for example). The frequency of human antibodies to a particular target in the natural human repertoire is typically orders of magnitude lower than in the repertoire of immunized mice. Accordingly, a high through-put technology capable of surveying millions of individual antibody-producing human B lymphocytes is needed. Since human B cells have a very limited lifetime ex vivo (under 10 days) and no method is known that can immortalize a substantial majority of such cells, the discovery technology must also operate within that time window.

The antibodies on which those of the invention are based were identified using the previously described CellSpot™ technology (U.S. Pat. Nos. 7,413,868 and 7,939,344, incorporated herein by reference). This assay method effectively shrinks an ELISA equivalent assay down to a virtual well of nearly single cell dimensions by capturing secreted IgG from a single cell as a footprint in the vicinity of the cell. In that way, 5 million B cells can be readily analyzed. Further, by use of microscopic multiplexing reagents (combinatorially colored fluorescent latex microspheres, cf U.S. Pat. No. 6,642,062, incorporated herein by reference), each cell's secreted antibody footprint can be characterized in detail for specificity and/or affinity using multiple biochemical probes. The fidelity of the quantitative assay is sufficient to enable rescue of extremely rare favorable cells from the survey population. The cloned antibody-encoding genes expressed in an exogenous cell typically show a phenotype consistent with the original identifying assay.

Fully human complete antibodies of the invention are distinct from those actually found in nature, as they are prepared recombinantly by constructing nucleic acids that encode a generic form of the constant region of heavy and/or light chain and further encode the relevant heterologous variable regions representative of human antibodies. Moreover, because the B cells are cultured prior to assay, mutations may arise during this ex vivo period of identification. Further, the low frequency of the desired B cells means that the antibody of interest is not present at a detectable (or recoverable) level in serum.

As used herein, the term "antibody" or "mAb" includes immunoreactive fragments of traditional antibodies or mAbs that still retain immunospecificity or antigen-binding such as Fab, F(ab')$_2$, F$_v$ fragments, and single-chain antibodies in which the variable regions of heavy and light chain are directly bound without some or all of the constant regions. Also included are bispecific antibodies which contain a heavy and light chain pair derived from one antibody source and a heavy and light chain pair derived from a different antibody source. Similarly, since light chains are often interchangeable without destroying specificity, antibodies composed of a heavy chain variable region that determines the specificity of the antibody combined with a heterologous light chain variable region are included within the scope of the invention. Chimeric antibodies with constant and variable regions derived, for example, from different species and species-ized forms are also included.

The critical amino acid sequences of the variable regions that determine specificity are the CDR sequences arranged on a framework which framework can vary without necessarily affecting specificity or decreasing affinity to an unacceptable level. Definition of these CDR regions is accomplished by art-known methods. Specifically, the most commonly used method for identifying the relevant CDR regions is that of Kabat as disclosed in Wu, T. T., et al., *J. Exp. Med.* (1970) 132:211 250 and Kabat, E. A., et al. (1983) *Sequence of Proteins of Immunological Interest*, Bethesda National Institute of Health, 323 pages. Another similar and commonly employed method is that of Chothia, published in Chothia, C., et al., *J. Mol. Biol.* (1987) 196:901 917 and in Chothia, C., et al., *Nature* (1989) 342:877 883. An additional modification has been suggested by Abhinandan, K. R., et al., *Mol. Immunol.* (2008) 45:3832 3839. The present invention includes the CDR regions as defined by any of these systems or other recognized systems known in the art.

The specificities of the binding of the mAbs of the invention are defined, as noted, by the CDR regions mostly those of the heavy chain, but complemented by those of the light chain as well (the light chains being somewhat interchangeable). Therefore, the mAbs of the invention may contain the three CDR regions of a heavy chain and optionally the three CDR's of a light chain that matches it. Because binding affinity is also determined by the manner in which the CDR's are arranged on a framework, the mAbs of the invention may contain complete variable regions of the heavy chain containing the three relevant CDR's as well as, optionally, the complete light chain variable region comprising the three CDR's associated with the light chain complementing the heavy chain in question. This is true with respect to the mAbs that are immunospecific for a single epitope as well as for bispecific antibodies or binding moieties that are able to bind two separate epitopes.

Bispecific binding moieties may be formed by covalently linking two different binding moieties with different specificities. Multiple technologies now exist for making a single antibody-like molecule that incorporates antigen specificity domains from two separate antibodies (bi-specific antibody). Suitable technologies have been described by MacroGenics (Rockville, Md.), Micromet (Bethesda, Md.) and Merrimac (Cambridge, Mass.). (See, e.g., Orcutt, K. D., et al., *Protein Eng. Des. Sel.* (2010) 23:221 228; Fitzgerald, J., et al., *MAbs.* (2011) 1:3; Baeuerle, P. A., et al., *Cancer Res.* (2009) 69:4941 4944.) For example, the CDR regions of the heavy and optionally light chain derived from one monospecific mAb may be coupled through any suitable linking means to peptides comprising the CDR regions of the heavy chain sequence and optionally light chain of a second mAb. If the linkage is through an amino acid sequence, the bispecific binding moieties can be produced recombinantly and the nucleic acid encoding the entire bispecific entity expressed recombinantly. As was the case for the binding moieties with a single specificity, the invention also includes the possibility of binding moieties that bind to one or both of the same epitopes as the bispecific antibody or binding entity/binding moiety that actually contains the CDR regions. The invention further includes bispecific constructs which comprise the complete heavy and light chain sequences or the complete heavy chain sequence and at least the CDR's of the light chains or the CDR's of the heavy chains and the complete sequence of the light chains.

As noted above, the mAbs of the invention are directed to members of the KIR family receptors.

Names of KIR family receptors are based on structure and include the number of extracellular immunoglobulin like domains (D) and the length (Long or Short) of the intracytoplasmic tail. A final digit is added to indicate the specific gene. Most of the KIR family members are inhibitory, but a few are stimulatory. Different combinations of these genes are expressed to varying degrees. Further balancing of inhibitory and stimulatory signaling arises from polymorphisms within the KIR genes, and from individual cells expressing only some of the KIR family members. About 50% of humans express a particular combination referred to as haplotype A, which encodes mostly inhibitory receptors: KIR2DL1-3 and KIR3DL1-3. Haplotype A also includes the activating receptors KIR2DS4 and KIR2DL4; however, KIR2DS4 lacks function in a majority of instances and many KIR2DL4 allelic gene products are not displayed on the cell surface.

The mAbs of the invention may be produced recombinantly using known techniques. Thus, with regard to the novel antibodies described herein, the invention also relates to nucleic acid molecules comprising nucleotide sequence encoding them, as well as vectors or expression systems that comprise these nucleotide sequences, cells containing expression systems or vectors for expression of these nucleotide sequences and methods to produce the binding moieties by culturing these cells and recovering the binding moieties produced. Any type of cell typically used in recombinant methods can be employed including prokaryotes, yeast, mammalian cells, insect cells and plant cells. Also included are human cells (e.g., muscle cells or lymphocytes) transformed with a recombinant molecule that encodes the novel antibodies.

Typically, expression systems for the mAbs of the invention include a nucleic acid encoding the protein coupled to control sequences for expression. In many embodiments, the control sequences are heterologous to the nucleic acid encoding the protein. The invention is thus directed to nucleic acids encoding any of the mAbs of the invention including the bispecific mAbs and to recombinant methods for their production, as described above.

The invention is also directed to pharmaceutical and veterinary compositions which comprise as active ingredients the mAbs of the invention. The compositions contain suitable physiologically compatible excipients such as buffers and other simple excipients or may be more complex formulations such as liposomal or delayed release formulations. The compositions may include additional active ingredients as well, in particular anti-tumor chemotherapeutic agents. The mAbs of the invention may also be used in diagnosis.

The mAbs and compositions thereof of the invention are useful in the treatment of tumors, including solid tumors and tumors of the blood as well as melanoma in humans and other subjects such as veterinary subjects as well as in conducting laboratory experiments such as those in rats or mice. The dosage required is variable and depends on the judgment of the attending practitioner. The skilled artisan will understand that depending on the condition as well as the physical characteristics of the subject to be treated the dose will be adjusted accordingly.

Conventional formulations with excipients, modes of administration and indications for treatment are described in U.S. Pat. No. 9,018,366, incorporated herein by reference, and are included in the invention.

Example 1

Human peripheral blood mononuclear cells (PBMC's) from anonymized donors from the Stanford Blood Center, obtained under informed consent, were screened for ICM targets, including KIR2DL3 using the CellSpot™ assay described in U.S. Pat. Nos. 7,413,868 and 7,939,344. B cells isolated from whole blood were stimulated with cytokines and mitogens to initiate a brief period of proliferation, differentiation and antibody secretion (lasting ~5 days) and plated for subjection to the assay. The encoding nucleic acids for the variable regions of positive antibodies were extracted and used to produce antibodies recombinantly by cloning the DNA into expression vectors that contain a signal peptide as well as fusion of the DNA encoding the variable region with DNA cloned independently that codes for the constant region of the antibody.

A survey of 22 blood donors for binding to different ICM antigens, including KIR2DL3 resulted in detection of anti-KIR antibodies in 19 of the 22 donors. BSA was used as a counterscreen to eliminate polyreactive antibodies. The four mAbs listed below were thus produced.

```
TRL8504 VH
                                             (SEQ.ID NO: 1)
QVQLVESGGGVVRPGRSLRLSCAASGFTFNRFAMHWVRQAPGKGLEWVSV

ISYDGHNKYYIDSVKGRFTISRDDSKNTLHLQMNSLRPEDTAVYYCARAR

DDGRGIFDYWGQGILVTVSS

TRL8504 VL (KAPPA)
                                             (SEQ.ID NO: 2)
DIVMTQSPDSLAVSLGERATINCKSSQSVLYSSNNRNYLAWYQRKPGQPP

KLLIYWASTRESGVPDRFSGSGSGTDFTLTISSLQAEDVAVYYCQQYHSI

PLTFGGGTKVEIKR

TRL8507 VH
                                             (SEQ.ID NO: 3)
QVQLVESGGGVVQPGRSLRLSCAASGFTFSNYGMHWVRQAPGKGLEWVAV

ISFDGGNKYYADSVKGRFTISRDNSKNTLYLQMNSLRAEDTAVYYCAKSG

YFDSSGYFYPYYYYGMDVWGQGTTVTVSS

TRL8507 VL (LAMBDA)
                                             (SEQ.ID NO: 4)
DIELTQAPSVSVSPGQTARITCSGDALPKEYAYWYQQKPGQAPVLVIYKD

SERPSGIPERFSGSSSGTTVTLTISGVQAEDEGDYYCQSADSSGTHVVFG

GGTKLTVL

TRL8605 VH
                                             (SEQ.ID NO: 5)
QVQLVQSGGGVVQPGRSLRLSCAVSGFTFSSYGMHWVRQAPGKGLEWVTI

ISYDGSNYDYADSVKGRFTISRDNSKNMVYLQMNSLRADDTAVYYCAKDG

FDYWGQGTLVTVSS

TRL8605 VL (KAPPA)
                                             (SEQ.ID NO: 6)
DIVLTQSPDSLAVSLGERATINCKSSQSVLYSSNNRTYLAWFQQKSGQPP

KLLIYWASTRQSGVADRFSGSGSGTDFTLTISSLQAEDVAVYYCQQYYTT

PFTFGPGTRVDFKR

TRL8608 VH
                                             (SEQ.ID NO: 7)
QVQLVQSGAEVKKPGASVKISCKASGYTFTSYYMHWLRQAPGQGLEWMGV

INPTDGSTSYAQKFHGRVTMTRVTSTSTVYMDLSSLRSDDTAMYYCAKAH

IHAAEGEWFDPWGQGTLVTVSS
```

TRL8608 VL (KAPPA)
(SEQ.ID NO: 8)
DIEMTQSPDSLAVSLGERATINCKSSQSVLYNSNNKNYLAWYQQKPGQPP
KLLIYWASTREFGVPDRFSGSGSGTDFTLTISSLQAEDVAVYYCQQYYSV
PWTFGQGTKVEIKR

The sequences of the forgoing were compared to those described for murine antibodies in U.S. Pat. No. 9,018,366. Two examples are designated 1-7F9 and 1-4F1. Compared to 1-7F9, TRL8605 VH gene is 51% identical in sequence (61% conserved), and VL is 62% identical (75% conserved). Compared to 1-4F1, TRL8605 VH gene is 51% identical in sequence (61% conserved), and VL is 59% identical (68% conserved).

Example 2

The mAbs prepared in Example 1 were tested in adsorption ELISA using different KIR Extracelullar Domains (ECD), either purchased or produced in house. Serial dilutions allowed calculating binding affinities (listed below in Table 1 in nM); ND: not detectable. TRL8605 shows sub-nM affinity to several KIR family members.

TABLE 1

| Affinity nM | TRL8504 | TRL8507 | TRL8605 | TRL8608 |
| --- | --- | --- | --- | --- |
| KIR2DL1 | ND | ND | 0.026 | 1100 |
| KIR2DL2 | 12 | 40 | 0.018 | 1800 |
| KIR2DL3 | 38 | 0.1 | 0.005 | 79 |
| KIR2DL4 | ND | ND | ND | 2000 |
| KIR3DL1 | 10 | ND | ND | 1900 |
| KIR3DL2 | ND | 67 | ND | ND |
| KIR3DL3 | ND | ND | ND | ND |
| KIR3DS1 | 54 | ND | ND | 1800 |
| KIR2DS4 | 55 | ND | 2.6 | Not tested |
| BSA | ND | ND | ND | ND |

The invention claimed is:

1. An isolated nucleic acid or isolated nucleic acids that separately or in combination encode a monoclonal antibody (mAb) that binds an extracellular portion of at least one inhibitory Killer IgG-like Receptor (KIR) family member selected from KIR2DL1, KIR2DL2, and KIR2DL3, said mAb comprising the CDRs of the heavy chain variable region of TRL 8605 (SEQ ID NO: 5), the CDRs of the light chain variable region of TRL 8605 (SEQ ID NO: 6), and a non-native constant region.

2. A recombinant vector or recombinant vectors containing the nucleic acid or nucleic acids of claim 1.

3. Cells containing the vector or vectors of claim 2.

4. A method to produce a mAb that binds to an extracellular portion of KIR which method comprises culturing the cells of claim 3 and recovering said mAb produced.

* * * * *